US008785145B2

(12) United States Patent
Mignon Godefroy et al.

(10) Patent No.: US 8,785,145 B2
(45) Date of Patent: Jul. 22, 2014

(54) METHOD FOR DIAGNOSING GRAM-NEGATIVE INFECTIONS

(75) Inventors: Karine Yvonne Gabrielle Mignon Godefroy, Paris (FR); Hélène Nuyttens, Ivry sur Seine (FR); Julie Roge, Montrouge (FR); Damien Yann Marie-Joseph Thomas, Chilly Mazarin (FR)

(73) Assignee: Ingen Biosciences, Chilly Mazarin (FR)

( * ) Notice: Subject to any disclaimer, the term of this patent is extended or adjusted under 35 U.S.C. 154(b) by 0 days.

(21) Appl. No.: 13/571,498

(22) Filed: Aug. 10, 2012

(65) Prior Publication Data

US 2013/0040320 A1    Feb. 14, 2013

Related U.S. Application Data

(60) Provisional application No. 61/522,513, filed on Aug. 11, 2011.

(30) Foreign Application Priority Data

Nov. 7, 2011   (EP) .................................... 11306444

(51) Int. Cl.
*G01N 33/53* (2006.01)
*G01N 33/00* (2006.01)

(52) U.S. Cl.
USPC ........................................ 435/7.92; 435/7.1

(58) Field of Classification Search
None
See application file for complete search history.

(56) References Cited

U.S. PATENT DOCUMENTS 7,704,697 B2    4/2010  Arie et al.

FOREIGN PATENT DOCUMENTS

| EP | 1769249 A2 | 4/2007 |
| EP | 1804061 A1 | 7/2007 |
| FR | 2878861 A1 | 6/2006 |
| WO | 2006010805 A2 | 2/2006 |
| WO | 2006104890 A2 | 10/2006 |
| WO | 2009138689 A2 | 11/2009 |

OTHER PUBLICATIONS

Greenspan et al. Nature Biotechnology 17:936-937, 1999.*
Skolnick et al. Trends in Biotechnology 18: 34-39, 2000.*
McGuinness et al. Mol. Microbiol. 7: 505-514, 1993.*
McGuinness et al. Lancet 337: 514-517, 1991.*
Achermann et al., "Improved Diagnosis of Periprosthetic Joint Infection by Multiplex PCR of Sonication Fluid from Removed Implants", Journal of Clinical Microbiology, Apr. 2010, pp. 1208-1214, vol. 48, No. 4.
Boswell, "Serological Cross Reaction Between Legionella and Campylobacter in the Rapid Microagglutination Test", Journal of Clinical Pathology, 1996, pp. 584-586, vol. 49, No. 7.
Costerton et al., "The Application of Biofilm Science to the Study and Control of Chronic Bacterial Infections", The Journal of Clinical Investigation, Nov. 2003, pp. 1466-1477, vol. 112, No. 10.
Gouriet et al., "Comparison of the New InoDiag Automated Fluorescence Multiplexed Antigen Microarray to the Reference Technique in the Serodiagnosis of Atypical Bacterial Pneumonia", Clinical Microbiology and Infection, 2008, pp. 1119-1127, vol. 14, No. 12.
Keasey et al., "Extensive Antibody Cross-Reactivity Among Infectious Gram-Negative Bacteria Revealed by Proteome Microarray Analysis", Molecular and Cellular Proteomics, Dec. 27, 2008, pp. 924-935, vol. 8, No. 5.
Moran et al., "The Diagnosis and Management of Prosthetic Joint Infections", Journal of Antimicrobial Chemotherapy, 2010, pp. 1145-1154, vol. 65, Suppl. 3.
Roux et al., "Diagnosis of Prosthetic Joint Infection by Beadmill Processing of a Periprosthetic Specimen", Clinical Microbiology and Infection, 2010, pp. 447-450, vol. 17, No. 3.
Schäfer et al., "Prolonged Bacterial Culture to Identify Late Periprosthetic Joint Infection: A Promising Strategy", Clinical Infectious Diseases, Dec. 1, 2008, pp. 1403-1409, vol. 47, No. 11.
Vinh et al., "Device-Related Infections: A Review", Journal of Long-Term Effects of Medical Implants, 2005, pp. 467-488, vol. 15, No. 5.
Extended European Search Report for corresponding EP Application No. 11306444.8, 12 pages, Mar. 2012.

* cited by examiner

*Primary Examiner* — S. Devi
(74) *Attorney, Agent, or Firm* — Thompson Coburn LLP

(57) ABSTRACT

The invention concerns an in vitro method for determining if an individual is infected by a gram-negative bacterium preferably on prosthesis comprising: (i) detection of antibodies directed against a polypeptide of sequence SEQ ID NO: 2 and antibodies directed against a polypeptide of sequence SEQ ID NO: 4, in a biological sample of the individual, and (ii) deduction therefrom that the individual is infected by a gram-negative bacterium. The invention further concerns the kit for diagnosing of such an infection.

9 Claims, No Drawings

SEQUENCE LISTING

```
<160> NUMBER OF SEQ ID NOS: 9

<210> SEQ ID NO 1
<211> LENGTH: 1098
<212> TYPE: DNA
<213> ORGANISM: Chlamydia pneumoniae

<400> SEQUENCE: 1
ctgcctgtag ggaacccttc tgatccaagc ttattaattg atggtacaat atgggaaggt      60
gctgcaggag atccttgcga tccttgcgct acttggtgcg acgctattag cttacgtgct     120
ggattttacg gagactatgt tttcgaccgt atcttaaaag tagatgcacc taaaacattt     180
tctatgggag ccaagcctac tggatccgct gctgcaaact atactactgc cgtagataga     240
```

-continued

```
cctaacccgg cctacaataa gcatttacac gatgcagagt ggttcactaa tgcaggcttc    300
attgccttaa acatttggga tcgctttgat gttttctgta ctttaggagc ttctaatggt    360
tacattagag gaaactctac agcgttcaat ctcgttggtt tattcggagt taaaggtact    420
actgtaaatg caaatgaact accaaacgtt tctttaagta acggagttgt tgaactttac    480
acagacacct ctttctcttg gagcgtaggc gctcgtggag ccttatggga atgcggttgt    540
gcaactttgg gagctgaatt ccaatatgca cagtccaaac ctaaagttga agaacttaat    600
gtgatctgta acgtatcgca attctctgta aacaaaccca agggctataa aggcgttgct    660
ttccccttgc aacagacgc tggcgtagca cagctactg gaacaaagtc tgcgaccatc    720
aattatcatg aatggcaagt aggagcctct ctatcttaca gactaaactc tttagtgcca    780
tacattggag tacaatggtc tcgagcaact tttgatgctg ataacatccg cattgctcag    840
ccaaaactac ctacagctgt tttaaactta actgcatgga accttctttt actaggaaat    900
gccacagcat tgtctactac tgattcgttc tcagacttca tgcaaattgt ttcctgtcag    960
atcaacaagt ttaaatctag aaaagcttgt ggagttactg taggagctac tttagttgat   1020
gctgataaat ggtcacttac tgcagaagct cgtttaatta acgagagagc tgctcacgta   1080
tctggtcagt tcagattc                                                  1098
```

<210> SEQ ID NO 2
<211> LENGTH: 366
<212> TYPE: PRT
<213> ORGANISM: Chlamydia pneumoniae

<400> SEQUENCE: 2

```
Leu Pro Val Gly Asn Pro Ser Asp Pro Ser Leu Leu Ile Asp Gly Thr
  1               5                  10                  15

Ile Trp Glu Gly Ala Ala Gly Asp Pro Cys Asp Pro Cys Ala Thr Trp
                 20                  25                  30

Cys Asp Ala Ile Ser Leu Arg Ala Gly Phe Tyr Gly Asp Tyr Val Phe
             35                  40                  45

Asp Arg Ile Leu Lys Val Asp Ala Pro Lys Thr Phe Ser Met Gly Ala
 50                  55                  60

Lys Pro Thr Gly Ser Ala Ala Asn Tyr Thr Thr Ala Val Asp Arg
 65                  70                  75                  80

Pro Asn Pro Ala Tyr Asn Lys His Leu His Asp Ala Glu Trp Phe Thr
                 85                  90                  95

Asn Ala Gly Phe Ile Ala Leu Asn Ile Trp Asp Arg Phe Asp Val Phe
            100                 105                 110

Cys Thr Leu Gly Ala Ser Asn Gly Tyr Ile Arg Gly Asn Ser Thr Ala
            115                 120                 125

Phe Asn Leu Val Gly Leu Phe Gly Val Lys Gly Thr Thr Val Asn Ala
130                 135                 140

Asn Glu Leu Pro Asn Val Ser Leu Ser Asn Gly Val Val Glu Leu Tyr
145                 150                 155                 160

Thr Asp Thr Ser Phe Ser Trp Ser Val Gly Ala Arg Gly Ala Leu Trp
                165                 170                 175

Glu Cys Gly Cys Ala Thr Leu Gly Ala Glu Phe Gln Tyr Ala Gln Ser
            180                 185                 190

Lys Pro Lys Val Glu Glu Leu Asn Val Ile Cys Asn Val Ser Gln Phe
            195                 200                 205

Ser Val Asn Lys Pro Lys Gly Tyr Lys Gly Val Ala Phe Pro Leu Pro
```

```
              210                 215                 220
Thr Asp Ala Gly Val Ala Thr Ala Thr Gly Thr Lys Ser Ala Thr Ile
225                 230                 235                 240

Asn Tyr His Glu Trp Gln Val Gly Ala Ser Leu Ser Tyr Arg Leu Asn
                245                 250                 255

Ser Leu Val Pro Tyr Ile Gly Val Gln Trp Ser Arg Ala Thr Phe Asp
                260                 265                 270

Ala Asp Asn Ile Arg Ile Ala Gln Pro Lys Leu Pro Thr Ala Val Leu
            275                 280                 285

Asn Leu Thr Ala Trp Asn Pro Ser Leu Leu Gly Asn Ala Thr Ala Leu
        290                 295                 300

Ser Thr Thr Asp Ser Phe Ser Asp Phe Met Gln Ile Val Ser Cys Gln
305                 310                 315                 320

Ile Asn Lys Phe Lys Ser Arg Lys Ala Cys Gly Val Thr Val Gly Ala
                325                 330                 335

Thr Leu Val Asp Ala Asp Lys Trp Ser Leu Thr Ala Glu Ala Arg Leu
                340                 345                 350

Ile Asn Glu Arg Ala Ala His Val Ser Gly Gln Phe Arg Phe
            355                 360                 365

<210> SEQ ID NO 3
<211> LENGTH: 435
<212> TYPE: DNA
<213> ORGANISM: Legionella pneumophila

<400> SEQUENCE: 3
gattgggcaa agataggcgt agttgattta caaaaaatca tgcaaacctc aaatcaaatg      60
aaggaaatcc aacagaagtt ggaaaaagaa tttaagcctc gtcgagacaa gcttgtcgca     120
atggaagcaa gcttgaaaag cgacatggaa aaattcaagc gtgatagtgc tataatgagc     180
gcgagccaaa agaaagaatt ggaaagaaa attgttgcgt cacaacaaca gtttgaacgt     240
gatggacaac aatatcagca agaattgagc acggctcaca tgaagctat ggaaggtctg      300 tataataagg ttcgtactgc cattaccaaa attgccaagg atgagaagta cgatattatt     360
gttcagaaag atgcagcgcc cttcagcagc gaatctcttg atgtaacaga taaagttatt     420
aaagcaatta attaa                                                      435

<210> SEQ ID NO 4
<211> LENGTH: 144
<212> TYPE: PRT
<213> ORGANISM: Legionella pneumophila

<400> SEQUENCE: 4

Asp Trp Ala Lys Ile Gly Val Val Asp Leu Gln Lys Ile Met Gln Thr
1               5                  10                  15

Ser Asn Gln Met Lys Glu Ile Gln Gln Lys Leu Glu Lys Glu Phe Lys
            20                  25                  30

Pro Arg Arg Asp Lys Leu Val Ala Met Glu Ala Ser Leu Lys Ser Asp
        35                  40                  45

Met Glu Lys Phe Lys Arg Asp Ser Ala Ile Met Ser Ala Ser Gln Lys
    50                  55                  60

Lys Glu Leu Glu Lys Lys Ile Val Ala Ser Gln Gln Gln Phe Glu Arg
65                  70                  75                  80

Asp Gly Gln Gln Tyr Gln Gln Glu Leu Ser Thr Ala His Asn Glu Ala
                85                  90                  95
```

-continued

```
Met Glu Gly Leu Tyr Asn Lys Val Arg Thr Ala Ile Thr Lys Ile Ala
            100                 105                 110

Lys Asp Glu Lys Tyr Asp Ile Ile Val Gln Lys Asp Ala Ala Pro Phe
        115                 120                 125

Ser Ser Glu Ser Leu Asp Val Thr Asp Lys Val Ile Lys Ala Ile Asn
    130                 135                 140

<210> SEQ ID NO 5
<211> LENGTH: 1332
<212> TYPE: DNA
<213> ORGANISM: Legionella pneumophila

<400> SEQUENCE: 5
acgtttgttt taaaggaatt tgatgcacta aaaagtcatt ttaacgacac cgttaaaatc      60
atccttcaac gcgaaaaaaa ggacaaaatt gaagaccttc ccaaccccag aaaagaagag     120
cttcaatttc tgaccgctgt tctcaatcaa ttggaagcaa aaatcgatga actgaaacca     180
cgttctttgg ccagctatgt ccatgtattt tatggtgcta tgctgcttgt ctgtaaagac     240
gttgaaaata atctgcgggt gatggaaaag aaagaaaaca gcttgctgtt tactcgctta     300
atggatggta tgggtatttc tgatgaaaat ataccaacat ctgagcagaa catcatgttt     360
tacagaggat taaacaaatt cttaaatttc atttatgaaa gcaatgattc tcgtaaaggc     420
ttaaaaaagg agcatttcct gcaagtcctt tcgttaaaaa agatatactc tttagccaaa     480
ttaagttatg agcaggaaga ggcagctgaa aataatgctt tggcaaaatt aactgctgat     540
ggaaaaacca aagccaatgc gaacagcttc catgtggaaa aaccaatcga ttcatccatt     600
gttgagcaat tcaaatcctg ggatgaaatg aaaggcgctc ttcatcaatt aattctcgat     660
gaactttctg ataagaacgt tgctaaaatt tcagctttaa gtcaagcccg ctccgcacaa     720
ctgaaatttt tacaaacgat ggcagaacaa ctagacaaga tccctaacca atctcttgag     780
ccgtctgaga aatggccat tcttgctgga gcaatgtata tcgttcgtgg ccaaatagcc     840
caggagtatg gaaaagatcc attaagcaac gataaaatca gcgctactgt gattcataca     900
ggtttaagca cgatacttca tgccaatgct gattgctgtg aagacaagga agtactgatt     960
gctgctgcga ataaatttat tcgtcatatg gttattgagc gtcctgaaca atcaaataaa    1020
aaaatcacta aggaatccgt tcgagaaaac aacatgtttt ccgacatcgc cggcttccaa    1080
ttgatctctg tcttgacgtt aatacaaaac atgatcaaaa catgtcgtac tgatgccatt    1140
gaagcttgtg tcaccaagcg taaggaagaa ctcgaagcat taaaacccaa aaaagagggt    1200
tattccattg cgagttcagt cactggatat gtaggcagct ggtttaaaaa agcaccaagc    1260
atgtctgaag aagacgaaga agatgactta aaagatcaaa acacagcaga agagaccagc    1320
aaaccgaccg ta                                                        1332

<210> SEQ ID NO 6
<211> LENGTH: 444
<212> TYPE: PRT
<213> ORGANISM: Legionella pneumophila

<400> SEQUENCE: 6

Thr Phe Val Leu Lys Glu Phe Asp Ala Leu Lys Ser His Phe Asn Asp
1               5                   10                  15

Thr Val Lys Ile Ile Leu Gln Arg Glu Lys Lys Asp Lys Ile Glu Asp
            20                  25                  30

Leu Pro Asn Pro Arg Lys Glu Glu Leu Gln Phe Leu Thr Ala Val Leu
        35                  40                  45
```

-continued

Asn Gln Leu Glu Ala Lys Ile Asp Glu Leu Lys Pro Arg Ser Leu Ala
 50                  55                  60

Ser Tyr Val His Val Phe Tyr Gly Ala Met Leu Val Cys Lys Asp
 65                  70                  75                  80

Val Glu Asn Asn Leu Arg Val Met Glu Lys Lys Glu Asn Ser Leu Leu
                 85                  90                  95

Phe Thr Arg Leu Met Asp Gly Met Gly Ile Ser Asp Glu Asn Ile Pro
                100                 105                 110

Thr Ser Glu Gln Asn Ile Met Phe Tyr Arg Gly Leu Asn Lys Phe Leu
                115                 120                 125

Asn Phe Ile Tyr Glu Ser Asn Asp Ser Arg Lys Gly Leu Lys Lys Glu
130                 135                 140

His Phe Leu Gln Val Leu Ser Leu Lys Lys Ile Tyr Ser Leu Ala Lys
145                 150                 155                 160

Leu Ser Tyr Glu Gln Glu Ala Ala Glu Asn Asn Ala Leu Ala Lys
                165                 170                 175

Leu Thr Ala Asp Gly Lys Thr Lys Ala Asn Ala Asn Ser Phe His Val
                180                 185                 190

Glu Lys Pro Ile Asp Ser Ser Ile Val Glu Gln Phe Lys Ser Trp Asp
                195                 200                 205

Glu Met Lys Gly Ala Leu His Gln Leu Ile Leu Asp Glu Leu Ser Asp
210                 215                 220

Lys Asn Val Ala Lys Ile Ser Ala Leu Ser Gln Ala Arg Ser Ala Gln
225                 230                 235                 240

Leu Lys Phe Leu Gln Thr Met Ala Glu Gln Leu Asp Lys Ile Pro Asn
                245                 250                 255

Gln Ser Leu Glu Pro Ser Glu Lys Met Ala Ile Leu Ala Gly Ala Met
                260                 265                 270

Tyr Ile Val Arg Gly Gln Ile Ala Gln Glu Tyr Gly Lys Asp Pro Leu
                275                 280                 285

Ser Asn Asp Lys Ile Ser Ala Thr Val Ile His Thr Gly Leu Ser Thr
290                 295                 300

Ile Leu His Ala Asn Ala Asp Cys Cys Glu Asp Lys Glu Val Leu Ile
305                 310                 315                 320

Ala Ala Ala Asn Lys Phe Ile Arg His Met Val Ile Glu Arg Pro Glu
                325                 330                 335

Gln Ser Asn Lys Lys Ile Thr Lys Glu Ser Val Arg Glu Asn Asn Met
                340                 345                 350

Phe Ser Asp Ile Ala Gly Phe Gln Leu Ile Ser Val Leu Thr Leu Ile
                355                 360                 365

Gln Asn Met Ile Lys Thr Cys Arg Thr Asp Ala Ile Glu Ala Cys Val
370                 375                 380

Thr Lys Arg Lys Glu Glu Leu Glu Ala Leu Lys Pro Lys Lys Glu Gly
385                 390                 395                 400

Tyr Ser Ile Ala Ser Ser Val Thr Gly Tyr Val Gly Ser Trp Phe Lys
                405                 410                 415

Lys Ala Pro Ser Met Ser Glu Glu Asp Glu Glu Asp Leu Lys Asp
                420                 425                 430

Gln Asn Thr Ala Glu Glu Thr Ser Lys Pro Thr Val
435                 440

<210> SEQ ID NO 7
<211> LENGTH: 419

-continued

<212> TYPE: PRT
<213> ORGANISM: Chlamydia pneumoniae

<400> SEQUENCE: 7

Met Ser Tyr Tyr His His His His His Leu Glu Ser Thr Ser Leu
1               5                   10                  15

Tyr Lys Lys Ala Gly Leu Leu Pro Val Gly Asn Pro Ser Asp Pro Ser
            20                  25                  30

Leu Leu Ile Asp Gly Thr Ile Trp Glu Gly Ala Ala Gly Asp Pro Cys
        35                  40                  45

Asp Pro Cys Ala Thr Trp Cys Asp Ala Ile Ser Leu Arg Ala Gly Phe
    50                  55                  60

Tyr Gly Asp Tyr Val Phe Asp Arg Ile Leu Lys Val Asp Ala Pro Lys
65                  70                  75                  80

Thr Phe Ser Met Gly Ala Lys Pro Thr Gly Ser Ala Ala Ala Asn Tyr
                85                  90                  95

Thr Thr Ala Val Asp Arg Pro Asn Pro Ala Tyr Asn Lys His Leu His
            100                 105                 110

Asp Ala Glu Trp Phe Thr Asn Ala Gly Phe Ile Ala Leu Asn Ile Trp
        115                 120                 125

Asp Arg Phe Asp Val Phe Cys Thr Leu Gly Ala Ser Asn Gly Tyr Ile
    130                 135                 140

Arg Gly Asn Ser Thr Ala Phe Asn Leu Val Gly Leu Phe Gly Val Lys
145                 150                 155                 160

Gly Thr Thr Val Asn Ala Asn Glu Leu Pro Asn Val Ser Leu Ser Asn
                165                 170                 175

Gly Val Val Glu Leu Tyr Thr Asp Thr Ser Phe Ser Trp Ser Val Gly
            180                 185                 190

Ala Arg Gly Ala Leu Trp Glu Cys Gly Cys Ala Thr Leu Gly Ala Glu
        195                 200                 205

Phe Gln Tyr Ala Gln Ser Lys Pro Lys Val Glu Glu Leu Asn Val Ile
    210                 215                 220

Cys Asn Val Ser Gln Phe Ser Val Asn Lys Pro Lys Gly Tyr Lys Gly
225                 230                 235                 240

Val Ala Phe Pro Leu Pro Thr Asp Ala Gly Val Ala Thr Ala Thr Gly
                245                 250                 255

Thr Lys Ser Ala Thr Ile Asn Tyr His Glu Trp Gln Val Gly Ala Ser
            260                 265                 270

Leu Ser Tyr Arg Leu Asn Ser Leu Val Pro Tyr Ile Gly Val Gln Trp
        275                 280                 285

Ser Arg Ala Thr Phe Asp Ala Asp Asn Ile Arg Ile Ala Gln Pro Lys
    290                 295                 300

Leu Pro Thr Ala Val Leu Asn Leu Thr Ala Trp Asn Pro Ser Leu Leu
305                 310                 315                 320

Gly Asn Ala Thr Ala Leu Ser Thr Thr Asp Ser Phe Ser Asp Phe Met
                325                 330                 335

Gln Ile Val Ser Cys Gln Ile Asn Lys Phe Lys Ser Arg Lys Ala Cys
            340                 345                 350

Gly Val Thr Val Gly Ala Thr Leu Val Asp Ala Asp Lys Trp Ser Leu
        355                 360                 365

Thr Ala Glu Ala Arg Leu Ile Asn Glu Arg Ala Ala His Val Ser Gly
    370                 375                 380

Gln Phe Arg Phe Tyr Pro Ala Phe Leu Tyr Lys Val Val Asp Ser Arg
385                 390                 395                 400

Leu Leu Thr Lys Pro Glu Arg Lys Leu Ser Trp Leu Leu Pro Pro Leu
            405                 410                 415

Ser Asn Asn

<210> SEQ ID NO 8
<211> LENGTH: 166
<212> TYPE: PRT
<213> ORGANISM: Legionella pneumophila

<400> SEQUENCE: 8

Met Ser Tyr Tyr His His His His His His Leu Glu Ser Thr Ser Leu
1 5 10 15

Tyr Lys Lys Ala Gly Leu Asp Trp Ala Lys Ile Gly Val Val Asp Leu
20 25 30

Gln Lys Ile Met Gln Thr Ser Asn Gln Met Lys Glu Ile Gln Gln Lys
35 40 45

Leu Glu Lys Glu Phe Lys Pro Arg Arg Asp Lys Leu Val Ala Met Glu
50 55 60

Ala Ser Leu Lys Ser Asp Met Glu Lys Phe Lys Arg Asp Ser Ala Ile
65 70 75 80

Met Ser Ala Ser Gln Lys Lys Glu Leu Glu Lys Lys Ile Val Ala Ser
85 90 95

Gln Gln Gln Phe Glu Arg Asp Gly Gln Gln Tyr Gln Gln Glu Leu Ser
100 105 110

Thr Ala His Asn Glu Ala Met Glu Gly Leu Tyr Asn Lys Val Arg Thr
115 120 125

Ala Ile Thr Lys Ile Ala Lys Asp Glu Lys Tyr Asp Ile Ile Val Gln
130 135 140

Lys Asp Ala Ala Pro Phe Ser Ser Glu Ser Leu Asp Val Thr Asp Lys
145 150 155 160

Val Ile Lys Ala Ile Asn
165

<210> SEQ ID NO 9
<211> LENGTH: 467
<212> TYPE: PRT
<213> ORGANISM: Legionella pneumophila

<400> SEQUENCE: 9

Met Ser Tyr Tyr His His His His His His Leu Glu Ser Thr Ser Leu
1 5 10 15

Tyr Lys Lys Ala Gly Leu Thr Phe Val Leu Lys Glu Phe Asp Ala Leu
20 25 30

Lys Ser His Phe Asn Asp Thr Val Lys Ile Ile Leu Gln Arg Glu Lys
35 40 45

Lys Asp Lys Ile Glu Asp Leu Pro Asn Pro Arg Lys Glu Glu Leu Gln
50 55 60

Phe Leu Thr Ala Val Leu Asn Gln Leu Glu Ala Lys Ile Asp Glu Leu
65 70 75 80

Lys Pro Arg Ser Leu Ala Ser Tyr Val His Val Phe Tyr Gly Ala Met
85 90 95

Leu Leu Val Cys Lys Asp Val Glu Asn Asn Leu Arg Val Met Glu Lys
100 105 110

Lys Glu Asn Ser Leu Leu Phe Thr Arg Leu Met Asp Gly Met Gly Ile
115 120 125

```
Ser Asp Glu Asn Ile Pro Thr Ser Glu Gln Asn Ile Met Phe Tyr Arg
    130                 135                 140

Gly Leu Asn Lys Phe Leu Asn Phe Ile Tyr Glu Ser Asn Asp Ser Arg
145                 150                 155                 160

Lys Gly Leu Lys Lys Glu His Phe Leu Gln Val Leu Ser Leu Lys Lys
                165                 170                 175

Ile Tyr Ser Leu Ala Lys Leu Ser Tyr Glu Gln Glu Glu Ala Ala Glu
            180                 185                 190

Asn Asn Ala Leu Ala Lys Leu Thr Ala Asp Gly Lys Thr Lys Ala Asn
        195                 200                 205

Ala Asn Ser Phe His Val Glu Lys Pro Ile Asp Ser Ser Ile Val Glu
    210                 215                 220

Gln Phe Lys Ser Trp Asp Glu Met Lys Gly Ala Leu His Gln Leu Ile
225                 230                 235                 240

Leu Asp Glu Leu Ser Asp Lys Asn Val Ala Lys Ile Ser Ala Leu Ser
                245                 250                 255

Gln Ala Arg Ser Ala Gln Leu Lys Phe Leu Gln Thr Met Ala Glu Gln
            260                 265                 270

Leu Asp Lys Ile Pro Asn Gln Ser Leu Glu Pro Ser Glu Lys Met Ala
        275                 280                 285

Ile Leu Ala Gly Ala Met Tyr Ile Val Arg Gly Gln Ile Ala Gln Glu
    290                 295                 300

Tyr Gly Lys Asp Pro Leu Ser Asn Asp Lys Ile Ser Ala Thr Val Ile
305                 310                 315                 320

His Thr Gly Leu Ser Thr Ile Leu His Ala Asn Ala Asp Cys Cys Glu
                325                 330                 335

Asp Lys Glu Val Leu Ile Ala Ala Asn Lys Phe Ile Arg His Met
            340                 345                 350

Val Ile Glu Arg Pro Glu Gln Ser Asn Lys Lys Ile Thr Lys Glu Ser
        355                 360                 365

Val Arg Glu Asn Asn Met Phe Ser Asp Ile Ala Gly Phe Gln Leu Ile
    370                 375                 380

Ser Val Leu Thr Leu Ile Gln Asn Met Ile Lys Thr Cys Arg Thr Asp
385                 390                 395                 400

Ala Ile Glu Ala Cys Val Thr Lys Arg Lys Glu Glu Leu Glu Ala Leu
                405                 410                 415

Lys Pro Lys Lys Glu Gly Tyr Ser Ile Ala Ser Ser Val Thr Gly Tyr
            420                 425                 430

Val Gly Ser Trp Phe Lys Lys Ala Pro Ser Met Ser Glu Glu Asp Glu
        435                 440                 445

Glu Asp Asp Leu Lys Asp Gln Asn Thr Ala Glu Glu Thr Ser Lys Pro
450                 455                 460

Thr Val Lys
465
```

METHOD FOR DIAGNOSING GRAM-NEGATIVE INFECTIONS

CROSS REFERENCE TO RELATED APPLICATIONS

This application claims the benefit of U.S. Provisional Application No. 61/522,513, filed Aug. 11, 2011, and claims priority under 35 USC §119 to European patent application EP 11306444.8, filed Nov. 7, 2011, both of which are incorporated herein by reference in their entireties.

INCORPORATION OF SEQUENCE LISTING

A Sequence Listing containing the file named "12P1872_SEQLIST_ST25.txt" which is 22,084 bytes (as measure in MS-Windows®) and created on Aug. 9, 2012, is incorporated herein by reference in its entirety. The Sequence Listing contains SEQ ID NOs: 1-9.

FIELD OF THE INVENTION

The present invention relates to a method of diagnosis of infections due to gram-negative bacteria preferably, of prosthetic joint infections. More particularly, the invention concerns an in vitro method for determining if an individual is infected by a gram-negative bacterium comprising: (i) detection of antibodies directed against a polypeptide of sequence SEQ ID NO: 2 and antibodies directed against a polypeptide of sequence SEQ ID NO: 4, in a biological sample of the individual, and (ii) deduction therefrom that the individual is infected by a gram-negative bacterium. The invention further concerns the kit for diagnosing of such an infection.

BACKGROUND OF THE INVENTION

There are approximately 10 million wearers of prosthetic joints in the world today, and the number of prosthetic joint surgeries continues to increase each year, mainly because of population aging and of the increasing prevalence of obesity, which leads to an excess weight borne by the joints. Accordingly, it is estimated that by 2020, 2.5 million individuals will undergo surgery to insert a prosthetic joint or to replace an existing prosthetic joint. Besides, an increase in the number of initial joint replacements done in young patients (i.e. under 50 years old) is also observed. Current figures indicate that approximately 430,000 total hip and knee replacements are done each year in the United States, while approximately 130,000 total hip replacements (THR) and 100,000 total knee replacements (TKR) are implanted or replaced each year in France, where there are currently more than one million wearers of prosthetic joints.

Infection is one of the main complications of joint replacement surgery. In spite of the considerable progress recorded over recent years, prosthetic joint infections are still common, hovering between 0.3% and 2% for total hip replacements, and between 0.5% and 5% for total knee replacements, with the highest rates of infection occurring when existing prosthetic joints are replaced (from 3 days to nearly 20 years following surgery, with an average of 20% of infections occurring within 3 months of joint replacement; 40% occurring between 3 months and 2 years; and 40% occurring after 2 years). These infections are associated with a non-negligible mortality rate (2.5%) as well as with a high morbidity. They usually require one or several additional surgeries and a long course of antibiotics, resulting in significant and often lengthy functional disability. Eventually, the cost of managing these complications is very high, estimated at approximately 60,000 euros per prosthetic joint infection, thereby multiplying by four the cost price of a prosthetic joint when an infection occurs, e.g. reaching a total cost of approximately 80,000 euros for an infected prosthetic hip joint.

Prosthetic joints become infected by two different pathogenetic routes: locally introduced and hematogenous types of osteomyelitis. The locally introduced form of infection is the result of wound sepsis contiguous to the prosthesis or operative contamination. Any bacteremia can induce infection of a total joint replacement by the hematogenous route. Genitourinary and gastrointestinal tract procedures or infections are associated with gram-negative bacillary, *Enterococci* and anaeobic infections of prostheses. The frequency of the presence of the specific etiologic microorganisms in prosthetic joint sepsis varies among the published studies, but a general view of the spectrum of this bacteriology and the prominence of certain microbial groups is known. *Staphylococci* (coagulase-negative *staphylococci* and *S. aureus*) are the principal causative agents; aerobic *streptococci* and gram-negative bacilli are each responsible for 20% to 25%, and anaerobes represent 10% of these infections. Recent study reported microbiologic findings of 53 episodes of gram-negative prosthetic joint infections occurring among patients treated during 2000-2006 with 19% of *Pseudomonas aeruginosa*, 10% *Escherichia coli*, 8% *Klebsiella pneumoniae*, 3% *Enterobacter cloacae*, 2% *Acinetobacter baumannii*, 2% *Salmonella enterica*, 2% *Haemophilus influenzae*, 1% *Proteus mirabilis*, 1% *Bacteroides fragilis* and 3% non identified for monomicrobial infections (Hsieh et al. (2009) Clin. Infect. Dis. 49: 1036-1043). Other prosthetic joint infections due to other gram-negative bacteria such as *Morganella morganii*, *Pasteurella multocida*, *Serratia marcescens*, *Brucella* spp., *Francisella tularensis*, *Neisseria elongata*, *Neisseria perflava*, *Citrobacter koseri*, *Yersinia enterolitica* were also reported [Navarro et al. (1997) J. Infect. 35: 192-194; Arslan et al. (1998) J. Infect. 37: 70-71; Pittman et al. (1996) Pediatr. Neurosurg. 24: 50-51; Cooper et al. (1999) Clin. Infect. Dis. 29(6): 1589-1591; Evans et al. (2007) J. Med. Microbiol. 56(Pt 6): 860-862; Clark et al. (1968) Annals of Internal Medicine 68: 2386-2389; Adam et al. (2010) The journal of arthroplasty in press; Pras et al. (1992) Postgrad. Med. J. 68(803): 762-763; Werno et al. (2002) J. Clin. Microbiol. 40(3): 1053-1055; Peterson et al. (1993) Clin. Infect. Dis. 16(3): 439-440)]. The spectrum of microbial agents capable of causing prosthetic joint infection is however unlimited and even includes organisms ordinarily considered "contaminants" of cultures, such as *Bacillus* spp.

Although gram-negative infections constitute a relatively minor proportions of prosthetic joint infections, they are of significant clinical importance, because treatment of such infections is considered more complicated as a result of virulence of the organisms, their growing resistance to antimicrobial agents, and the comorbid conditions of patients (Mc-Donald et al. (1989) J. Bone Joint Surg. Am. 71: 828-834; Legout et al. (2006) Clin. Microbiol. Infect. 12: 1030-1036; Schurman et al. (1978) Clin. Orthop. Relat. Res. 134: 268-274).

The gold standard for diagnosing prosthesis infection remains bacteriological analysis, which involved isolation and culture of the infecting bacteria at the site of infection, from relevant samples. Bacteriological analysis is generally considered as significant if at least 2 joint aspirate or intraoperative tissue specimens for culture or if at least 1 intraoperative culture is positive for gram-negative bacteria, plus if there is evidence of infection at the site of prosthesis with presence of a discharging sinus communicating with the joint, operative findings of purulence, or positive laboratory and histopathological test results (Mirra et al. (1976) Clin. Orthop. Relat. Res. 117: 221-240). Several drawbacks are however associated to bacteriological analysis. Conventional detection methods rely on the evidencing of the bacteria on direct examination of the pathological specimen. It is therefore possible that a pathological specimen is not detected by direct microscopic examination of this pathological specimen. Moreover, obtaining pre-operative samples or aspiration liquids for subsequent culture is an invasive procedure which usually requires a surgical procedure carried out under general anesthesia. Secondly, the specificity is often insufficient, since contaminant microorganisms may be isolated. Besides, positive results can be hindered due to the initiation of treatment with antibiotics. Thirdly, no standardized techniques have been established for culturing the samples and interpreting the results from the cultures.

There are currently no other methods for establishing the diagnosis of gram-negative bacteria prosthesis infection. Thus the object of this invention proposes an alternative technique for the diagnosis of the gram-negative prosthetic joint infections. A serological approach based on the antibodies of anti gram-negative bacteria could overcome the drawbacks associated to bacteriological analysis.

SUMMARY OF THE INVENTION

The present invention arises from the unexpected identification, by the inventors, that the particular combination of proteins 14D3 of *Chlamydia pneumoniae* (herein after SEQ ID NO: 2) and 2E1 of *Legionella pneumophila* (herein after SEQ ID NO: 4) providing for efficient detection of anti gram-negative bacteria antibodies in biological samples.

Thus, the present invention relates to a method, in particular an in vitro method, for determining if an individual is infected by a gram-negative bacterium comprising:

detection of antibodies directed against a polypeptide of sequence SEQ ID NO: 2 and antibodies directed against a polypeptide of sequence SEQ ID NO: 4, in a biological sample of the individual, and deduction therefrom that the individual is infected by a gram-negative bacterium.

According to said method, when antibodies directed against a polypeptide of sequence SEQ ID NO: 2 and antibodies directed against a polypeptide of sequence SEQ ID NO: 4 are detected in a biological sample of an individual, said individual is infected by a gram-negative bacterium. Inversely, if no antibody directed against a polypeptide of sequence SEQ ID NO: 2 and no antibody directed against a polypeptide of sequence SEQ ID NO: 4 is detected in a biological sample of an individual, said individual is not infected by a gram-negative bacterium.

Detection of antibodies directed either against a polypeptide of sequence SEQ ID NO: 2 or against a polypeptide of sequence SEQ ID NO: 4 in a biological sample of an individual is not sufficient to assess that said individual is infected by a gram-negative bacterium. Indeed, while the inventors demonstrated that detection of antibodies directed against a polypeptide of sequence SEQ ID NO: 2 or SEQ ID NO: 4 provides for a diagnosis of patients that have been infected by gram-negative bacteria with a high sensibility, said diagnosis has a very low specificity. Surprisingly, detection of antibodies directed against polypeptide of sequences SEQ ID NO: 2 and of antibodies directed against polypeptide of sequence SEQ ID NO: 4 provides for a diagnosis of patients infected by gram-negative bacteria with a high sensibility and a high specificity. Indeed, the inventor demonstrated that by detecting antibodies directed against the polypeptides of sequences SEQ ID NO: 2 and SEQ ID NO: 4, the specificity of the diagnosis was unexpectedly increased by 17%. Antibodies directed against a polypeptide of sequence SEQ ID NO: 2 may recognize a protein containing or comprising said polypeptide of sequence SEQ ID NO: 2 or at least a fragment of said polypeptide of sequence SEQ ID NO: 2. Equally, antibodies directed against a polypeptide of sequence SEQ ID NO: 4 may recognize a protein containing or comprising said polypeptide of sequence SEQ ID NO: 4 or at least a fragment of said polypeptide of sequence SEQ ID NO: 4

Preferably, said detection of antibodies directed against a polypeptide of sequence SEQ ID NO: 2 and antibodies directed against a polypeptide of sequence SEQ ID NO: 4, in a biological sample of the individual comprises contacting the biological sample with at least one of:

(i) a polypeptide of sequence SEQ ID NO: 2; and/or, (ii) an homologous polypeptide comprising or consisting of a sequence having at least 90% identity with sequence SEQ ID NO: 2; and/or, (iii) a fragment of said polypeptide defined in (i) and/or fragment of said homologous polypeptide sequence defined in (ii), and, at least one of:

(iv) a polypeptide of sequence SEQ ID NO: 4; and/or, (v) an homologous polypeptide comprising or consisting of a sequence having at least 90% identity with sequence SEQ ID NO: 4; and/or, (vi) a fragment of said polypeptide defined in (iv) and/or fragment of said homologous polypeptide defined in (v);

provided the homologous polypeptide sequences defined in (ii) and (v) and the fragments defined in (iii) and (vi) can be bound by antibodies directed against a polypeptide of sequence SEQ ID NO: 2 or SEQ ID NO: 4.

Preferably said fragments defined in (iii) and (vi) may comprise 4 to 200 contiguous amino acids of said polypeptides defined in (i) and (iv) and/or of said homologous polypeptides defined in (ii) and (v).

As appropriate, a polypeptide comprising or consisting of sequence SEQ ID NO: 2 or SEQ ID NO: 4, and/or an homologous polypeptide comprising or consisting of a sequence having at least 90% identity with sequence SEQ ID NO: 2 or SEQ ID NO: 4 and/or a fragment comprising amino acids of said polypeptide of sequence SEQ ID NO: 2 or SEQ ID NO: 4 may be used for detection of antibodies directed against a polypeptide of sequence SEQ ID NO: 2 and antibodies directed against a polypeptide of sequence SEQ ID NO: 4. The one skilled in the art understand that for diagnosing a gram negative bacterium according to said method, at least a polypeptide of sequence SEQ ID NO: 2 or a fragment of sequence SEQ ID NO: 2 or an homologous polypeptide of sequence SEQ ID NO: 2 may be used in combination with at least a polypeptide of sequence SEQ ID NO: 4 or a fragment of sequence SEQ ID NO: 4 or an homologous polypeptide of sequence SEQ ID NO: 4.

As also appropriate, an individual may be considered as being infected by a gram-negative bacterium if antibodies directed against a first polypeptide comprising or consisting of sequence SEQ ID NO: 2 and a second polypeptide comprising or consisting of sequence SEQ ID NO: 4 are detected in a biological sample of said individual. Equally, if antibodies directed against a first homologous polypeptide comprising or consisting of a sequence having at least 90% identity with sequence SEQ ID NO: 2 and a second homologous polypeptide comprising or consisting of a sequence having at least 90% identity with sequence SEQ ID NO: 4; or antibodies directed against a first fragment of said polypeptide of sequence SEQ ID NO: 2 and a second fragment of said polypeptide of sequence SEQ ID NO: 4 are detected. Equally, an individual may be considered as being infected by a gram-negative bacterium if antibodies directed against a polypeptide comprising or consisting of sequence SEQ ID NO: 2 and an homologous polypeptide comprising or consisting of a sequence having at least 90% identity with sequence SEQ ID NO: 4; or antibodies directed against a polypeptide comprising or consisting of sequence SEQ ID NO: 2 and a fragment of an homologous polypeptide comprising or consisting of a sequence having at least 90% identity with sequence SEQ ID NO: 4; or antibodies directed against a polypeptide comprising or consisting of sequence SEQ ID NO: 2 and a fragment of a polypeptide of sequence SEQ ID NO: 4 are detected in biological sample of said individual. This is transposable when antibodies directed against a polypeptide of sequence SEQ ID NO: 2 are directed against a polypeptide fragment of SEQ ID NO: 2 or an homologous polypeptide sequence of SEQ ID NO: 2.

The present invention also relates to the use of:

(i) at least one polypeptide of sequence SEQ ID NO: 2 and/or SEQ ID NO: 4; and/or, (ii) at least one homologous polypeptide comprising or consisting of a sequence having at least 90% identity with sequence SEQ ID NO: 2 or SEQ ID NO: 4; and/or, (iii) at least one fragment of said polypeptide sequence defined in (i) and/or at least one fragment of said homologous polypeptide sequence defined in (ii), provided the homologous polypeptide defined in (ii) or the fragment defined in (iii) can be bound by antibodies directed a against polypeptide of sequence SEQ ID NO: 2 or SEQ ID NO: 4, for in vitro diagnosis of infection with a gram-negative bacterium by detecting antibodies directed against polypeptide of sequences SEQ ID NO: 2 and SEQ ID NO: 4, preferably by detecting antibodies directed against a polypeptide of sequence SEQ ID NO: 2 and antibodies directed against a polypeptide of sequence SEQ ID NO: 4.

Preferably, the fragment may comprise at least 4 to 200 contiguous amino acids of said polypeptide sequences defined in (i) and/or of said homologous polypeptide sequences defined in (ii), preferably 5 to 100.

The present invention also relates to a kit for diagnosing an infection by a gram-negative bacterium by detection of antibodies directed against a polypeptide of sequence SEQ ID NO: 2 and antibodies directed against a polypeptide of sequence SEQ ID NO: 4 comprising:

at least one of:

(i) a polypeptide of sequence SEQ ID NO: 2; and/or, (ii) an homologous polypeptide comprising or consisting of a sequence having at least 90% identity with sequence SEQ ID NO: 2; and/or, (iii) a fragment of said polypeptide defined in (i) and/or fragment of said homologous polypeptide defined in (ii), and, at least one of:

(iv) a polypeptide of sequence SEQ ID NO: 4; and/or, (v) an homologous polypeptide comprising or consisting of a sequence having at least 90% identity with sequence SEQ ID NO: 4; and/or, (vi) a fragment of said polypeptide defined in (iv) and/or fragment of said homologous polypeptide defined in (v);

provided the homologous polypeptide sequences defined in (ii) and (v) and the fragments defined in (iii) and (vi) can be bound by antibodies directed against a polypeptide of sequence SEQ ID NO: 2 or SEQ ID NO: 4

The present invention also related to an in vitro method, for determining if an individual is infected by a gram-negative bacterium comprising:

contacting capture ligands specific of a polypeptide of sequence SEQ ID NO: 2 and capture ligands specific of a polypeptide of sequence SEQ ID NO: 4, with a biological sample of the individual;

determining if said polypeptide of sequence SEQ ID NO: 2 is bound to the capture ligands specific of a polypeptide of sequence SEQ ID NO: 2 and said polypeptide of sequence SEQ ID NO: 4 is bound to the capture ligands specific of a polypeptide of sequence SEQ ID NO: 4;

deducing therefrom that the individual is infected by a gram-negative bacterium.

In an embodiment of the invention, the above-defined method comprises contacting specific capture ligands of polypeptide sequences comprising SEQ ID NO: 2 and SEQ ID NO: 4.

The present invention also relates to the use, in particular the in vitro use, of specific capture ligands, in particular an antibody, directed against a polypeptide of sequence SEQ ID NO: 2 and a capture ligands, in particular an antibody, directed against a polypeptide of sequence SEQ ID NO: 4 for determining if an individual is infected by a gram-negative bacterium, in an individual, in whom one detects the presence of at least an antigen of the aforesaid bacterium in a biological sample of the individual using a ligand of capture, in particular an antibody, directed against a polypeptide of sequence SEQ ID NO: 2 and a ligand of capture, in particular an antibody, directed against a polypeptide of sequence SEQ ID NO: 4. Said capture ligands directed against the polypeptide of sequence SEQ ID NO: 2 and said capture ligands directed against the polypeptide of sequence SEQ ID NO: 4 may be the same capture ligand such as for example, a common binding partner. An identical or different detecting mean may be used for detecting the binding of the capture ligand to sequence SEQ ID NO: 2 and sequence SEQ ID NO: 4.

The present invention also relates to an antigenic kit for diagnosing an infection by a gram-negative bacterium comprising a capture ligands, in particular an antibody, directed against a polypeptide of sequence SEQ ID NO: 2 and a capture ligands, in particular an antibody, directed against a polypeptide of sequence SEQ ID NO: 4.

DETAILED DESCRIPTION OF THE INVENTION

As intended herein, the expression "gram negative bacterium" or "gram negative bacteria", relates to a bacterium or to bacteria that do not retain violet coloration (commonly gentian violet or violet cristal dye) in the Gram staining protocol. During the Gram stain test, a counterstain (commonly fuchsin or safranin) is added after, coloring all Gram-negative bacteria with a red or pink color. Gram-positive bacteria will retain the violet coloration when washed in a decolorizing solution. The test itself is useful in classifying two distinct types of bacteria based on the structural differences of their bacterial cell walls. Indeed, by opposite to gram-positive bacteria, gram-negative bacteria have a lipopolysaccharide layer in their outer cell walls.

Preferably, the gram negative bacteria form bacterial biofilms.

Gram negative bacteria are composed of different phyla. Preferably, said gram-negative bacterium according to the invention may be selected from the group consisting of the proteobacteria phylum or the bacteroidetes phylum. Probacteria phylum is composed by different classes, preferably, gram-negative bacterium according to the invention may be a proteobacterium selected from the group consisting of alpha-proteobacteria, beta-proteobacteria, gamma-proteobacteria, or epsilon-proteobacteria classes. More preferably according to the invention, said gram-negative bacterium may be selected from the group consisting of Thiotrichales, Rhizobiales, Pseudomonadales, Neisseriales Campylobacterales, Pasteurellales orders. Even more preferably, said gram-negative bacterium may be selected from the group consisting of bacteria of the *Campylobacter*, *Pseudomonadaceae*, Neisseriaceae, Brucellaceae, Francisellaceae, *Enterobacteriaceae* and *Pasteurellaceae* families.

Preferably, said gram-negative bacterium is *Pseudomonas aeruginosa, Enterobacter amnigenus, Enterobacter aerogenes, Escherichia coli, Klebsiella pneumoniae, Klebsiella oxytoca, Acinetobacter baumannii, Salmonella enterica, Haemophilus influenzae, Proteus mirabilis, Bacteroides fragilis, Serratia marcescens, Morganella morganii, Francisella*

*tularensis, Brucella* spp., *Neisseria elongata, Neisseria perflava, Citrobacter koseri, Yersinia* spp., *Campylobacter* spp. or *Pasteurella multocida*.

In a particular embodiment of the invention, the gram-negative bacterium is not a gram-negative bacterium causing respiratory infections such as *Chlamydia pneumoniae, Legionella pneumophila, Bordetella pertussis* as these bacteria are not implicated prosthetic joint infections.

As intended herein, the expression 'infected' or 'infection' relates to individuals carrying a gram-negative bacterium as defined above. Preferably, the infection is a surface associated infection or a biofilm-associated infection. Infections by a gram-negative bacterium can occur by bacterial biofilms. Preferably, the infected individuals present one or more sites of infection wherein multiplication of the bacterium is occurring. Infections by a gram-negative bacterium can occur as a consequence of the contact of internal tissues with a foreign material contaminated by a gram-negative bacterium, in particular in a hospital setting. Accordingly, as intended herein, the infection preferably arises from the implantation of a prosthetic material in the individual, such as prosthetic joint, notably selected from the group consisting of a knee joint, a shoulder joint and a hip joint. Thus, the infection may be a device-associated-infection. Said device may be a medical device implanted in an individual such as prosthesis. Indeed, the infection may be a prosthetic or a periprosthetic infection and notably a periprosthetic joint infection.

Accordingly, as intended herein, the method according to the invention is implemented in order to determine if an individual suffers from an infection by a gram-negative bacterium, the mentioned infection being selected among an infection on prosthesis (in particular articular) such as a periprosthetic joint infection, an osteo-articular infection, a post-operative infection (in particular during the installation of a foreign material such as a prosthesis), a dental infection, a parodontite, a conjunctivitis, an endophtalmy, a cerebral abscess, an empyema under-dural, a lung infection, a peritonitis, an osteomyelitis, a septic arthritis, an endocarditis (in particular on prosthesis), a meningitis (in particular on shunts).

The individual can moreover be an individual diabetic, and/or presenting an immunodepression, and/or suffering of a cancer and/or carrying prosthetic material or catheter. Preferably the individual presenting a prosthetic joint selected from the group consisting of a knee joint, a shoulder joint and a hip joint. According to the invention, such a prosthetic joint may be infected by said a gram-negative bacterium.

As intended herein, the expression 'biological sample' includes both the sample as taken and the sample which has been subjected to various treatments after sampling, in particular to render it suitable for the use in the processes and methods according to the invention. The 'biological sample' according to the invention can be of any type liable to contain antibodies. However, it is preferred that the biological sample is selected from the group consisting of blood, serum, plasma, mucosa-associated lymphoid tissue (MALT), cerebrospinal fluid, articular liquid, pleural liquid, saliva, and urine.

As intended herein, the expression 'determining if an individual is infected by a gram-negative bacterium' encompasses establishing a diagnosis or diagnosing an infection by a gram-negative bacterium in an individual. It also encompasses following-up of individuals having undergone a surgical operation for implanting, cleaning or replacing the prosthesis. It further encompasses following the evolution of infection by a gram-negative bacterium, in particular within the framework of a therapeutic treatment. Accordingly, it is preferred that the individual is under treatment by antibiotics.

Determining if antibodies directed against a polypeptide of sequence SEQ ID NO: 2 and antibodies directed against a polypeptide of sequence SEQ ID NO: 4, are present in a biological sample of the individual can be carried out by various methods well known to one of skill in the art. However, determining if antibodies directed against a polypeptide of sequence SEQ ID NO: 2 and antibodies directed against a polypeptide of sequence SEQ ID NO: 4, are present in a biological sample of the individual comprises:

contacting the biological sample with:

(i) at least one polypeptide of sequence SEQ ID NO: 2 or SEQ ID NO: 4; and/or, (ii) at least one homologous sequence comprising or consisting of a sequence having at least 90% identity with sequences SEQ ID NO: 2 and/or SEQ ID NO: 4; and/or, (iii) at least one fragment of said polypeptide sequence defined in (i) and/or at least one fragment of said homologous polypeptide sequence defined in (ii), the fragment of said polypeptide sequences defined in (i) and/or of said homologous polypeptide sequences defined in (ii);

provided the homologous polypeptide sequence defined in (ii) or the fragment defined in (iii) can be bound by antibodies directed against polypeptide of sequence SEQ ID NO: 2 or SEQ ID NO: 4.

detecting antibodies, preferably IgG, directed against a polypeptide of sequence SEQ ID NO: 2 and antibodies directed against a polypeptide of sequence SEQ ID NO: 4 bound to said polypeptide of sequences SEQ ID NO: 2 and/or SEQ ID NO: 4, to said homologous sequence or to said at least one fragment.

The polypeptide of sequences SEQ ID NO: 2 and/or SEQ ID NO: 4; the homologous sequences thereto, or the fragments thereof, can present either as polypeptide chains resulting from the in vivo, ex vivo or in vitro polymerization of amino acids selected from the 20 natural amino acids, or as modified polypeptide chains. As intended herein, in vivo or ex vivo polymerization notably encompasses production by in vitro translation or by chemical synthesis. Where the polypeptide is modified, it can results from the use of non-natural amino acids during the in vivo, ex vivo or in vitro polymerization of the polypeptide chain and from post-polymerisation modifications. The polypeptide can be modified one or several times by identical or different modifications. The modifications can be anywhere in the polypeptide chain, and notably in the peptide backbone, in the amino acid lateral groups, or at the N-terminal or C-terminal extremities of the polypeptide chain. Modification notably encompass acylation, in particular acetylation, palmytoylation, glypiation, prenylation and myristoylation, ADP-ribosylation, amidation, covalant linkage of a lipid, such as phosphatidylinositol, flavin, an heme, or a nucleotide, covalent, or non-covalent cross-linking, cyclisation, disulfide bridge oxidation and reduction, methylation and demethylation, pyroglutamate formation, formylation, gamma-carboxylation, glycosylation, hydroxylation, iodation, phosphorylation, selenoylation, sulfatation, racemisation, addition of amino-acids, such as arginylation, or of polypeptides, such as ubiquitinylation (Proteins structure and molecular properties, 2nd ed., T. E. Creighton, W. H. Freeman and Company, New York (1993) and Wold, F., Posttranslational Protein Modifications: Prospects and Prospective customers, pgs 1-12 in Covalent post-translational modification of proteins, B. C. Johnson, ED., Press Academy, New York (1983); Seifter et al. (1990) Meth. Enzymol. 182: 626-646 and Rattan et al. (1992) Protein Synthesis: Posttranslational Modifications and Aging, Ann. NR. Y. Acad. Sci. 663: 48-62).

Besides, where they are obtained by recombining means, the polypeptide chain comprising or consisting of sequence SEQ ID NO: 2 or SEQ ID NO: 4, the homologous polypeptide chain thereto, and the fragments thereof, may also comprise sequences useful for protein purification (so-called purification tags), such as polyhistidine tags, and optionally a sequence enabling the cleavage of these tags, such as protease cleavage sites.

Preferably, the polypeptide comprising a sequence selected from the group consisting of SEQ ID NO: 2 and SEQ ID NO: 4, comprises 350, 400, 500, or 1000 amino-acids at the most. More preferably the polypeptides comprising sequences selected from the group consisting of SEQ ID NO: 2 and SEQ ID NO: 4, are respectively encoded by nucleic acids comprising or consisting of SEQ ID NO: 1 and SEQ ID NO: 3.

The percentage of identity according to the invention can be calculated by methods well-known to one of skill in the art. The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

The term "homologous protein" or "homologous polypeptide" means a protein or a polypeptide having a percentage of identity with polypeptide of sequences SEQ ID NO: 2 and SEQ ID NO: 4 according to the invention.

Preferably, the percentage of identity relates to the number of identical amino-acids obtained for an optimal paired alignment (i.e. the alignment maximizing the number of identical amino-acids) of the sequence of a protein or a polypeptide homologous to SEQ ID NO: 2 and SEQ ID NO: 4, divided by the total number of amino-acids in SEQ ID NO: 2 or 4. Alignment can be performed manually or using computer programs such as the EMBOSS-Needle program (Needleman and Wunsch (1970) J. Mol. Biol. 48:443-453). Preferably, the percentage of identity according to the invention is at least 85%, more preferably from at least 90%, and even more preferably from at least 95%. Preferably, the fragment contains an epitope. The smaller fragment that may be recognized by an antibody may have 4 to 5 contiguous amino acids. Consequently, according to the invention a 'fragment' may be of 4, 5, 6, 7, 8, 9, 10, 11, 12, 13, 14, 15, 16, 17, 18, 19, 20 contiguous amino acids. Preferably, said fragment may comprise 22 to 200 contiguous amino acids, more preferably 25 to 150 contiguous amino acids, and more preferably 30 to 100 contiguous amino acids. Preferably also, the 'fragment' may comprise 35 to 80 contiguous amino acids, more preferably 40 to 75 contiguous amino acids at the most, and most preferably 45 to 70 contiguous amino acids at the most. Preferably also, the 'fragment' according to the invention consists of a portion of a sequence selected from the group consisting of SEQ ID NO: 2 and SEQ ID NO: 4, or of a portion of sequences presenting at least 85%, more preferably at least 90%, and more preferably from at least 95% of sequence SEQ ID NO: 2 or SEQ ID NO: 4.

As intended herein, the homologous polypeptide as defined above and the at least one fragment as defined above can be bound by at least one antibody directed against a protein comprising a sequence selected from the group consisting of SEQ ID NO: 2 and SEQ ID NO: 4. In other words, the homologous polypeptide as defined above and the at least one fragment as defined above comprises at least one of the epitopes of a polypeptide consisting of a sequence selected from the group consisting of SEQ ID NO: 2 and SEQ ID NO: 4. Accordingly, the homologous polypeptide as defined above and the at least one fragment as defined above comprise at least one of the epitopes of a protein comprising a sequence selected from the group consisting of SEQ ID NO: 2 and SEQ ID NO: 4. Accordingly, the homologous polypeptide as defined above and the at least one fragment as defined above should preferably be such that they provide at least 70%, more preferably at least 80% and most preferably at least 90%, of the sensitivity provided by the polypeptide comprising or consisting of sequences selected from the group consisting of SEQ ID NO: 2 and SEQ ID NO: 4, measured in the same conditions.

As intended herein, the term 'sensitivity' is defined as the percentage of individuals infected by a gram-negative bacterium, which biological samples, such as serum samples, are determined to contain antibodies directed against a polypeptide of sequence SEQ ID NO: 2 and antibodies directed against a polypeptide of sequence SEQ ID NO: 4, detectable according to the invention. The determining of the sensitivity provided by an antigen can be carried out according to various methods well-known to one of skill in the art and notably as illustrated in the following Example 1. Preferably, the antibodies detected in the biological samples according to the invention are IgG.

In addition, as that will appear clearly to one of skill in the art, "antibodies directed against polypeptide of sequences SEQ ID NO: 2 and SEQ ID NO: 4", "antibodies directed against a polypeptide of sequence SEQ ID NO: 2 and antibodies directed against a polypeptide of sequence SEQ ID NO: 4" or "antibodies directed against a protein comprising the sequence selected from the group consisting of sequences SEQ ID NO: 2 and SEQ ID NO: 4" means any antibody of the individual able to recognize a protein or a polypeptide consisting of sequences selected from the group consisting of SEQ ID NO: 2 and SEQ ID NO: 4, i.e. a specific antibody of this protein, but which can also recognize:

a larger protein comprising a sequence selected from the group consisting of SEQ ID NO: 2 and SEQ ID NO: 4; or a homologous protein comprising or consisting of a sequence having at least 90% identity with sequences selected from the group consisting of SEQ ID NO: 2 and SEQ ID NO: 4;

a fragment of at least 5, preferably 6 to 200 contiguous amino acids of homologous protein or a protein comprising or consisting of a sequence selected from the group consisting of SEQ ID NO: 2 and SEQ ID NO: 4.

Providing the detection of antibodies directed against polypeptides sequences comprising or consisting of sequences SEQ ID NO: 2 and SEQ ID NO: 4, in the biological samples, or the antigen detection of a gram-negative bacterium using a ligand of capture, such as an antibody, directed, preferably specifically, against polypeptide of sequences SEQ ID NO: 2 and SEQ ID NO: 4, can be easily implemented by one of skill in the art.

Being the detection of antibody directed against polypeptide sequences comprising or consisting of sequences SEQ ID NO: 2 and SEQ ID NO: 4 or, antibodies directed against a polypeptide of sequence SEQ ID NO: 2 and antibodies directed against a polypeptide of sequence SEQ ID NO: 4, in the biological samples, it can be carried out with the assistance at least one of (i) at least one protein comprising or consisting sequences SEQ ID NO: 2; or (ii) at least one homologous protein comprising sequence having at least 90% identity with sequence SEQ ID NO: 2; or (iii) at least one fragment of protein defined in (i) or homologous protein defined in (ii), and at least one of (vi) at least one protein comprising or consisting sequences SEQ ID NO: 4; or (v) at least one homologous protein comprising sequence having at least 90% identity with sequence SEQ ID NO: 4; or (vi) at least one fragment of protein defined in (vi) or homologous protein defined in (v).

Preferably said fragments comprise at least 5 contiguous amino acids of said protein defined in (i) and (vi) or homologous protein defined in (ii) and (v).

Preferably, in the above-defined method, detecting antibodies can be carried out with specific detecting ligands of the antibodies.

As intended herein, a "ligand" is a compound liable to specifically bind to a target, such as an antibody or an antigen. The ligand can be of any type but preferably, it is an antibody, an aptamer, or a peptide obtained by phage display. To determine whether antibodies or antigens are fixed by a ligand of capture one can use a ligand detection, which can be specific either antibodies or antigens fixed, or of the ligands of capture.

The methods calling upon ligands of capture and ligands of detection are well-known to one of skill of the art, and can be performed according to various well-known formats, solid or homogeneous phase, one or two stages, using a method sandwich or by competition. Preferably, the ligand of capture is immobilized on a solid phase, such as the walls of a well of a plate of microtitration or paramagnetic balls.

As intended herein, an "antigen" relates to any substance that triggers the production of an antibody by the immune system in an animal, including a human. Antigen refers also to a substance which is a ligand of an antibody to which it binds. The term "epitope" as used herein means the portion of the antigen which interacts with an antibody. When the antigen is a protein, said portion may be a specific amino acid sequence, a modified amino acid sequence, or a protein secondary or tertiary structure.

An "antibody" as intended herein relates to antibodies belonging to any species, such as human, mouse, rat, rabbit, goat, or camelidae species. The antibody can also be a chimeric antibody, i.e. an antibody which comprises parts originating from different species. Preferred chimeric antibodies are so-called "humanized" antibodies, wherein the constant parts (CH and CL) are of human origin and the variable parts (VH and VL) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')2, scFv fragments as well as camelidae single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) Nature 346:818-822 and Bock et al. (1992) Nature 355:564-566. The aptamers of a peptide nature and the production thereof are described, in particular, by Hoppe-Seyler et al. (2000) J. Mol Med. 78:426-430.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott and Smith (1990) Science 249:386-390, and Marks et al. (1991) J. Mol. Biol. 222:581-597. Preferably, the polypeptide obtainable by phage display is an scFv-type polypeptide (single-chain variable fragment). This technique is described, in particular, by Winter et al. (1994) Annu. Rev. Immunol. 12:433-455.

The term "specific", when it refers to recognition of a ligand or binding of a ligand to a first target, such as an antigen or an antibody, means that the ligand interacts with the first target without interacting substantially with another target which does not structurally resemble the first target, for example, the ligand. Preferably the antibody directed against a polypeptide of sequence SEQ ID NO: 2 or SEQ ID NO: 4 does not bind to a polypeptide having less than 85%, preferably 90%, sequence identity with SEQ ID NO:2 or SEQ ID NO:4, as appropriate.

As defined herein, the term "binds specifically" or similar terms, when used in the context of an antibody binding a target epitope, refers to the antibody having specificity for the target epitope (as opposed to other epitopes). The specificity need not be 100%. In one embodiment, the specificity is about 75% or greater (i.e., 75% specificity for the epitope). This means that about 75% of the antibodies that bind to an epitope will bind to the target epitope and about 25% of the antibodies will bind non-specifically. In another embodiment, the specificity is about 90% or greater.

In the above-defined method, determining if the capture ligands are respectively bound to an antigen can be carried out by using a detection ligand which is specific of said antigen but preferably binds to said antigen by recognition of an another binding site (i.e. epitope) than the recognition site of said capture ligand.

Preferably, the "detection ligand" according to the invention means marking or labeling molecules for detecting the ligand. The term 'marking' or "labeling" refers both to a direct labelling and to an indirect labelling (for example, by means of other ligands, themselves directly labelled, or using reagents of a labelled "affinity pair", such as, but not exclusively, the labelled avidin-biotin pair, etc.). Preferably, the label is a radioisotope, an enzyme or a fluorophore.

As will be clear to one of skill in the art, in the above-defined method, the proteins comprising sequence SEQ ID NO: 2 or SEQ ID NO: 4, the homologous proteins or the fragments can be used as a capture antigen.

Methods using capture antigens or ligands and detection ligands are well known to one of skill in the art and can be carried out in accordance with various well-known formats, for example in solid or homogeneous phase, in one or two steps, by a sandwich method or by a competitive method.

Preferably, the capture antigen or ligand is immobilised on a solid phase. By way of non-limiting examples of solid phase, microplates could be used, in particular polystyrene microplates, solid optionally paramagnetic particles or beads, or even polystyrene or polypropylene test tubes, glass, plastic or silicon chips, etc.

Although having distinct significances, the terms comprising, 'containing', and 'consisting of' were used in an interchangeable way in the description of the invention, and can be replaced one by the other.

The invention will be further described in view of the following examples.

Summary of the sequences described herein:

| Sequence description | SEQ ID NO: |
| --- | --- |
| 14D3 nucleotide sequence | 1 |
| 14D3 protein sequence | 2 |
| 2E1 nucleotide sequence | 3 |
| 2E1 protein sequence | 4 |
| 2A1 nucleotide sequence | 5 |
| 2A1 protein sequence | 6 |
| 14D3 + His tag protein sequence | 7 |
| 2E1 + His tag protein sequence | 8 |
| 2A1 + His tag protein sequence | 9 |

EXAMPLES

Example 1

Materials and Methods

Antigens 14D3 (SEQ ID NO: 7), 2E1 (SEQ ID NO: 8) and 2A1 (SEQ ID NO: 9) were recombinantly produced in

*Escherichia coli* and purified according to usual methods, such as described in Lavallie (1995) "Production of recombinant proteins in *Escherichia coil*". Unit 5.1. Current Protocols in Protein Science; Scopes (1995) "Strategies for protein purification" Unit 1.2. Current Protocols in Protein Science.

First screening was performed by high throughput ELISA. ELISA plates were coated overnight with 0.5 µg/mL of purified antigens 14D3 and 2E1 and with commercial lipopolysaccharide LPS (Sigma Aldrich). The plates were further saturated 2 hours with PBS-TWEEN containing 4% serum albumin bovine (SAB). Hundred microliters of each serum sample of patients or controls were added at a 1/100 dilution for 30 minutes. Human peroxydase-labeled anti-IgG antibody was then added for 30 minutes before revelation with tetrabenzimidine (TMB) for approximately 15 minutes. Sulphuric acid (100 µL) were then added in each well to stop the reaction. The 450 nm absorbance of each well was then measured after 5 minutes. Are regarded as 'positive' in ELISA, the serums identified by their binding to polypeptides (antigens) such as defined according to the invention.

Antigens 14D3 and 2E1 were then tested with technology LUMINEX® Antigen 2A1 (previously described in the diagnosis of *Legionella pneumophila* respiratory infections) was simultaneously tested to compare results. Briefly, the antigens were covalently attached to surface carboxyl groups of MAGPLEX MICROSPHERES (LUMINEX®) using N-hydroxysulfosuccinimide (sulfo-NHS) and 1-ethyl-3-(3-dimethylaminopropyl) carbodiimide hydrochloride (EDC) according the manufacturer's instructions. 50 µg were used for attachment to 5,000,000 microspheres. Detection of serum antibodies was carried out according to the manufacturer's instructions. Briefly, antigen-coupled microspheres were added to the wells of a multiwell plate and contacted with the various sera for a time sufficient to allow antibody-antigen complexes to be formed. After discarding the unreacted serum and washing the plate, a phycoerythrin-labeled anti-IgG antibody was added to the microspheres. Antibody-antigen complexes were further revealed by determining the mean fluorescence intensity (MFI) for each serum with a LUMINEX® analyzer.

The cut-off values for each serologic assay were determined by Receiver Operating Characteristics (ROC) curve analysis as described in the guideline GP10-A of December 1995 from the National Committee for Clinical Laboratory Standards (NCCLS) as the values yielding a maximum efficiency. The efficiency is defined as the ratio of the sum of the true positive samples and the true negative samples obtained with the serologic assays by the total number of samples assayed. True positive and negative samples are samples which are respectively determined as being positive and negative both using the serologic assay of the invention and bacteriological analysis. A sample was then considered positive if the antibody titer exceeded the defined cut-off value. The antigen combination was analyzed by discriminate function analysis before setting a cut-off value by ROC curve analysis as indicated above.

Example 2

Use of Polypeptides of the Invention for the Detection of Antibody in Serum Samples: First Screening by High Throughput ELISA The panel of samples tested is consisted of serum samples of 6 patients suffering from gram-negative bacteria prosthetic joint infections wherein the infection with *Escherichia coli* (n=2), *Klebsiella oxytoca* (n=1), *Serratia marcescens* (n=2), *Klebsiella pneumoniae* (n=1) was diagnosed positive with culture of 2 or more samplings on the infected prostheses. Control sera were collected from 2 healthy prosthesis carriers with no clinical sign of infection since at least 2 years.

The results of the 14D3 antigen was compared to commercial LPS results. The LPS is the major component of gram negative outer membrane and has been described as antigenic in many publications focusing on gram-negative bacteria infections.

TABLE 1

Results (ELISA) obtained by testing of the antigens

| | Antigens tested | |
|---|---|---|
| Ratio of positive sera | 14D3 | LPS |
| Gram-negative bacteria prosthesis positive patients (6) | 100% | 50% |
| Healthy prosthesis carriers (2) | 0% | 0% |

Table 1 shows the results obtained according to the invention for polypeptides 14D3 (SEQ ID NO: 2), and commercial LPS with secondary antibodies recognizing the immunoglobulins G present in serum samples of gram negative infected prosthesis patients or healthy prosthesis carriers.

Results show that polypeptides of the invention 14D3 (SEQ ID NO: 2) can be used for the diagnosis of infections of gram-negative bacteria infection on articular prostheses. The LPS also tested does not allow the diagnosis of such infections with any sufficient sensitivity and/or specificity.

Example 3

Diagnosis Potency of the Combination of 14D3 and 2E1 Polypeptides of the Invention for the Diagnosis of Gram-Negative Bacteria Infections on Prosthesis with Panels of Serums Samples and Control Serum Samples: Second Evaluation by LUMINEX® Technology. Comparison to Results with Combinations with 2A1 Polypeptide Previously Described

TABLE 2

Results (LUMINEX ® technology) obtained by testing of the selected antigens alone or in combination.

| | Tested antigens | | | | | |
|---|---|---|---|---|---|---|
| Ratio of positive sera | 14D3 | 2E1 | 2A1 | 14D3-2E1 | 2E1-2A1 | 14D3-2A1 |
| *Enterobacter* genus positive patients (6) | 100% | 100% | 67% | 100% | 50% | 50% |
| *Escherichia coli* positive patients (5) | 80% | 80% | 80% | 80% | 80% | 80% |

TABLE 2-continued

Results (LUMINEX ® technology) obtained by testing of the selected antigens alone or in combination.

| Ratio of positive sera | Tested antigens | | | | | |
|---|---|---|---|---|---|---|
| | 14D3 | 2E1 | 2A1 | 14D3-2E1 | 2E1-2A1 | 14D3-2A1 |
| *Klebsiella oxytoca* positive patient (1) | 100% | 100% | 0% | 100% | 0% | 0% |
| *Serratia marcescens* positive patients (2) | 100% | 100% | 100% | 100% | 50% | 100% |
| *Pseudomonas aeruginosa* positive patients (2) | 100% | 100% | 50% | 50% | 50% | 50% |
| *Pasteurella multocida* positive patient (1) | 100% | 100% | 100% | 100% | 100% | 100% |
| Total number of prosthesis infected patients (17) | 94% | 94% | 71% | 88% | 59% | 65% |
| *Bordetella pertussis* infected patients (15) | 40% | 73% | 47% | 40% | 33% | 20% |
| *Chlamydia* genus infected patients (15) | 93% | 93% | 73% | 93% | 73% | 73% |
| *Legionella pneumophila* infected patients (3) | 100% | 100% | 100% | 100% | 100% | 100% |
| Total number of other gram negative infected patients (33) | 82% | 70% | 64% | 70% | 58% | 52% |
| Healthy prosthesis carriers (31) | 42% | 32% | 39% | 10% | 19% | 16% |
| Healthy blood donors (39) | 38% | 26% | 15% | 5% | 8% | 8% |
| Infected prosthesis patients with other infections than gram-negative bacteria (13) | 46% | 54% | 38% | 23% | 23% | 8% |
| Total of control sera (83) | 41% | 33% | 28% | 10% | 14% | 11% |

The panel of samples tested consists of serum samples of 21 patients suffering from gram-negative bacteria prosthetic joint infections wherein the infection with *Enterobacter* genus (n=6, 1 *E. amnigenus*, 5 *E. cloacae*), with *Escherichia coli* (n=5), with *Klebsiella oxytoca* (n=1), with *Serratia marcescens* (n=2), with *Pseudomonas aeruginosa* (n=2) and with *Pasteurella multocida* (n=1) was diagnosed positive with culture of 1 or more samplings on the infected prostheses. Patients with gram negative respiratory infections to *Bordetella pertussis* (n=15), *Chlamydia* genus (n=15, 13 *C. pneumonia*, 2 *C. trachomatis*) and *Legionella pneumophila* (n=3) were also tested. Control sera were collected from (i) 31 healthy prosthesis carriers with no clinical sign of infection since at least 2 years, from (ii) 39 healthy blood donors and from (iii) 13 patients with prosthesis infections other than gram-negative bacteria prosthesis infections; i.e. *Propionibacterium acnes* (n=1), *Propionibacterium granulosum* (n=1), *Staphylococcus aureus* (n=2), *Staphylococcus epidermidis* (n=5), coagulase negative *staphylococci* (n=1), *Streptococcus dysgalactiae* (n=1), *Streptococcus anginosus* (n=1), *Streptococcus mitis* (n=1).

The results show a significant antibody response (the probability associated with a test of $X^2$ is lower than 0.05) against the polypeptides 14D3 and 2E1 identified according to the invention during the infections due to gram-negative bacteria. The results with 2A1 antigen are lower. However, only the 14D3-2E1 combination is shown to be of interest since it allows a 23-31% increase in specificity (41% and 33% of the control sera are detected with 14D3 or 2E1 alone vs. 10% with the 14D3-2E1 combination) with a good sensitivity. Surprisingly, the combination 14D3-2E1 according to the invention provides the diagnosis of a larger scope of infections than the combinations 14D3-2A1 or 2E1-2A1. Moreover, for identical bacterial infections, the 14D3-2A1 and 2E1-2A1 combinations do not allow the diagnosis of such infections with any sufficient sensitivity and specificity.

In conclusion, it appears impossible to predict the sensitivity and specificity, in particular an increase of the specificity, of a combination of antigens in view of their individual sensitivities and specificities. Besides, the 14D3-2E1 combination presents unexpected diagnosis potency for the diagnosis of infections due to gram-negative bacteria.

What is claimed is:

1. An in vitro method of determining if an individual is infected by a gram-negative bacterium, the method comprising:
    (a) detecting antibodies specific to the polypeptide of SEQ ID NO: 2 and antibodies specific to the polypeptide of SEQ ID NO: 4 in a biological sample of the individual, wherein the biological sample is selected from the group consisting of blood, serum, and plasma, and
    (b) deducing therefrom that the individual is infected by the gram-negative bacterium, wherein said infection is a biofilm-associated infection and the gram-negative bacterium is from a family selected from the group consisting of *Enterobacteriaceae, Pasteurellaceae,* and *Pseudomonadaceae*.

2. The method of claim 1, wherein said infection is a prosthetic infection in said individual.

3. The method of claim 1, wherein the antibodies are IgG.

4. The method of claim 1, wherein said gram-negative bacterium is *Pseudomonas aeruginosa, Escherichia coli, Klebsiella oxytoca, Enterobacter cloacae, Enterobacter amnigenus, Serratia marcescens,* and *Pasteurella multocida*.

5. The method of claim 1, wherein a prosthetic joint implanted in the individual is infected by said gram-negative bacterium.

6. The method of claim 1, wherein a prosthetic joint implanted in the individual is infected by said gram-negative bacterium, said prosthetic joint being selected from the group consisting of a knee joint, a shoulder joint and a hip joint.

7. The method of claim 1, wherein the detection of the antibodies specific to the polypeptide of sequence SEQ ID NO: 2 and the antibodies specific to the polypeptide of sequence SEQ ID NO: 4 comprises contacting the biological sample with the polypeptide of SEQ ID NO: 2 and the polypeptide of SEQ ID NO: 4.

8. The method of claim 1, wherein the individual is under antibiotic treatment.

9. An in vitro method of determining if an individual is infected by a gram-negative bacterium, the method comprising:
- (a) contacting capture ligands specific to a polypeptide of the amino acid sequence SEQ ID NO: 2 and capture ligands specific to a polypeptide of the amino acid sequence SEQ ID NO: 4 with a biological sample of the individual, wherein the biological sample is selected from the group consisting of blood, serum, and plasma;
- (b) determining if said polypeptide of the amino acid sequence SEQ ID NO: 2 is bound to the capture ligands specific to the polypeptide of the amino acid sequence of SEQ ID NO: 2 and if said polypeptide of the amino acid sequence SEQ ID NO: 4 is bound to the capture ligands specific to the polypeptide of the amino acid sequence SEQ ID NO: 4; and
- (c) deducing therefrom that the individual is infected by the gram-negative bacterium, wherein said infection is a biofilm-associated infection and the gram-negative bacterium is from a family selected from the group consisting of *Enterobacteriaceae, Pasteurellaceae*, and *Pseudomonadaceae*.

* * * * *